United States Patent
Sugiyama et al.

(10) Patent No.: US 9,714,455 B2
(45) Date of Patent: Jul. 25, 2017

(54) METHOD FOR DETECTING NUCLEIC ACID AMPLIFICATION IN SAMPLE AND DEVICE THEREFOR

(75) Inventors: Kimikazu Sugiyama, Hitachinaka (JP); Masato Ishizawa, Hitachinaka (JP); Yoshiyuki Shoji, Mito (JP); Minoru Sano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 252 days.

(21) Appl. No.: 13/810,954

(22) PCT Filed: Jul. 4, 2011

(86) PCT No.: PCT/JP2011/065250
§ 371 (c)(1),
(2), (4) Date: Jan. 18, 2013

(87) PCT Pub. No.: WO2012/011379
PCT Pub. Date: Jan. 26, 2012

(65) Prior Publication Data
US 2013/0130229 A1    May 23, 2013

(30) Foreign Application Priority Data
Jul. 21, 2010   (JP) ................................ 2010-163684

(51) Int. Cl.
*C12Q 1/68*      (2006.01)
*B01L 7/00*      (2006.01)
(Continued)

(52) U.S. Cl.
CPC ........... *C12Q 3/00* (2013.01); *G01N 35/0092* (2013.01); *G01N 35/026* (2013.01); *G01N 35/04* (2013.01); *B01L 7/52* (2013.01)

(58) Field of Classification Search
USPC ...................................................... 435/287.2
See application file for complete search history.

(56) References Cited

U.S. PATENT DOCUMENTS

2002/0155619 A1    10/2002   Kurihara et al.
2006/0204997 A1     9/2006   Macloszek et al.
(Continued)

FOREIGN PATENT DOCUMENTS

JP          6-327476 A     11/1994
JP        2002-318192 A    10/2002
(Continued)

OTHER PUBLICATIONS

Deiman B, van Aarle P, Sillekens P. Characteristics and applications of nucleic acid sequence-based amplification (NASBA). Mol Biotechnol. Feb. 2002; 20(2):163-79. Review.*

(Continued)

*Primary Examiner* — Young J Kim
(74) *Attorney, Agent, or Firm* — Crowell & Moring LLP

(57) ABSTRACT

A device for detecting nucleic acid amplification in a sample, comprising: a loading unit (thermoregulation unit) which is provided with a plurality of holes for loading reaction containers and capable of arbitrarily controlling a measurement unit for measuring samples in the containers that are loaded in the holes. The loading unit and the measurement unit, which are placed opposite to each other, can be operated independently from each other. In a transfer operation, the operation speeds of the thermoregulation unit and measurement unit are controlled so that the sum of these speeds amounts to an arbitrary constant value.

4 Claims, 12 Drawing Sheets

(51) Int. Cl.
    *C12Q 3/00*     (2006.01)
    *G01N 35/02*    (2006.01)
    *G01N 35/04*    (2006.01)
    *G01N 35/00*    (2006.01)

(56) References Cited

U.S. PATENT DOCUMENTS

| | | |
|---|---|---|
| 2007/0184548 A1 | 8/2007 | Tan et al. |
| 2009/0221059 A1 | 9/2009 | Williams et al. |
| 2010/0112567 A1* | 5/2010 | Adolfsen et al. ............. 435/6 |
| 2011/0104703 A1 | 5/2011 | Maeda et al. |
| 2011/0256532 A1* | 10/2011 | Sano et al. ............. 435/6.1 |

FOREIGN PATENT DOCUMENTS

| | | | | |
|---|---|---|---|---|
| JP | WO2010073917 | * | 7/2010 | ............ G01N 21/78 |
| JP | WO2010086943 | * | 8/2010 | ............ G01N 35/04 |
| WO | WO 02/16546 A1 | | 2/2002 | |
| WO | WO 2008/030914 A2 | | 3/2008 | |
| WO | WO 2008/057375 A2 | | 5/2008 | |
| WO | WO 2009/157353 A1 | | 12/2009 | |

OTHER PUBLICATIONS

"LightCycler® 480 Real-Time PCR System", Roche Applied Science, Sep. 2005, pp. 1-6, Roche Diagnostics GmbH. (Six (6) pages).
European Search Report dated Apr. 16, 2014 (six pages).
International Search Report including English translation dated Sep. 13, 2011 (Two (2) pages).

* cited by examiner

METHOD FOR DETECTING NUCLEIC ACID AMPLIFICATION IN SAMPLE AND DEVICE THEREFOR

TECHNICAL FIELD

The present invention relates to a method and a device for detecting nucleic acid amplification for a sample, in particular, which are suitable to automate a task therefor.

BACKGROUND ART

Recently, a demand for conducting a generic test using nucleic acid amplification has increased in a wide range of fields such as a clinical examination filed including infectious disease examination, a food field, and an environmental inspection field. Along with this, many test methods and test reagents have been developed for various test applications.

A test method used for detection of nucleic acid amplification includes PCR (polymerase chain reaction) and nucleic acid sequence-based amplification (NASBA).

In nucleic acid amplification, a temperature condition for amplification of nucleic acid varies for each of protocols specifying types of target nucleic acid and amplification techniques. The nucleic acid sequence-based amplification is carried out at a fixed temperature for nucleic acid amplification. On the other hand, PCR requires a temperature cycle of periodically varying the temperature of a sample by setting a plurality of temperature regions, so when the temperature cycle is repeated a given number of times, a nucleic acid amplification process is finished. In realtime PCR, a detection process for measurement (for example, fluorescent measurement) of nucleic acid amplification is further performed during the nucleic acid amplification process. An apparatus for automating processes of such nucleic acid amplification and detection performs a measurement operation for nucleic acid amplification while performing the temperature cycle for nucleic acid amplification, and then, after the temperature cycle was repeated by a given number of times as specified by a protocol, analysis with the processes is finished.

As a prior art for automating nucleic-acid amplification and detection, for example, Non-Patent Document 1 discloses an apparatus that has a plate holding a plurality of samples, and controls the temperature of the entire plate to be uniform.

This apparatus is of a batch processing type; hence, even if the apparatus has any empty loading position for a sample container, no sample can be added halfway after start of analysis.

In such a case, therefore, additional analysis must be started after completion of previous analysis, resulting in much time for obtaining the results.

Patent Document 1 discloses a technique, in which a sample holder is fixedly provided to hold a plurality of reaction containers each containing a sample and a reagent, and an optical sensor rotationally performs fluorescence detection of nucleic acid amplification in the reaction containers with fluorochrome-labeling. The technique, however, does not allow a new reaction container to be randomly loaded in a measurement section during measurement of a sample as in the above.

CITATION LIST

Patent Document

[Patent Document 1] Japanese Unexamined Patent Application Publication No. 2002-318192.

Non-Patent Document

[Non-patent Document 1] LightCycler (registered trade name) 480 from Roche.

SUMMARY OF THE INVENTION

Problems that the Invention is to Solve

For automation of a detection device for nucleic acid amplification, a loading unit that can load a plurality of sample containers (reaction containers) each containing a reaction solution (a sample and a reagent) containing nucleic acid, and has a thermoregulation unit for nucleic acid amplification, a measurement unit (for example, fluorescence detector) for detecting nucleic acid amplification in a loaded reaction container, and a conveyance unit that conveys each reaction container to the loading unit are commonly provided.

Assuming such an automation technique, in the existing techniques (including the apparatus configurations proposed in Patent Document 1 and Non-Patent Document 1), when a plurality of samples are concurrently analyzed with protocols specifying different required time periods (for example, when temperature cycle conditions for nucleic acid amplification of the samples can be independently controlled), a sample requiring short process time cannot be extracted before completion of temperature cycle control and measurement of any of other samples, resulting in considerably long standby time. In addition, while analysis has been executed, a new sample (sample) cannot be added, and an added sample cannot be analyzed without suspending analysis being executed.

The reason for such issues is as follows: the existing devices are adapted for batch processing, and thus one or more additional samples cannot be loaded singly or in series into a testing section (a position at which a loading unit and a measurement unit are located) in an interruptive manner for temperature control along an independent temperature program. This has prevented speedup of the test, and a measure for an emergency patient, such as an immediate test of the sample of the patient.

Moreover, when a plurality of samples have test items, reagents to be used, temperature programs, and/or other conditions being different from one another, measurement signals have been received from the samples at different points of timing, making it difficult to detect nucleic acid amplification in parallel by means of a common measurement unit.

An object of the present invention is to provide a nucleic-acid amplification detection device, which enables loading and analysis (nucleic-acid amplification detection) of one or more additional samples singly or in series without suspending a step of analysis being executed, in contrast to the existing nucleic-acid amplification detection device of a batch processing type, and provide a method of controlling the nucleic-acid amplification detection device.

Another object of the invention is to provide a nucleic-acid amplification detection device enabling concurrent analysis (nucleic-acid amplification detection of samples) of a plurality of samples, which have test items, reagents to be used, temperature programs, and/or other conditions being different from one another, with a common loading unit and a common measurement unit regardless of batch-processed nucleic-acid amplification or randomly-added nucleic-acid amplification.

Means for Solving the Problems

To achieve the above-described objects, the present invention is configured as follows.

(1) First, a method or device for detecting nucleic acid amplification, which uses a loading unit that can load a plurality of reaction containers for nucleic acid amplification, each reaction container containing a sample and a reagent, and has a thermoregulation unit capable of thermoregulation for nucleic acid amplification, and a measurement unit that is disposed facing the loading unit, and measures a reaction in the loaded reaction containers, the measurement unit which is configured to make a repeat of rotational movement or linear movement in a predetermined direction relative to the loading unit to sequentially receive measurement signal from each of the samples in the reaction containers loaded in the loading unit at timing in a fixed period, is characterized in that each of the loading unit and the measurement unit has an independent movement mechanism, and thereby, when loading of a new reaction container is requested during measurement of a previously loaded reaction container, relative movement velocity of the measurement unit with respect to the loading unit is controlled to be maintained constant with the movement mechanism without any difference from relative movement velocity before the request for new loading, and movement of the loading unit is concurrently controlled to allow any one of empty loading positions to reach a fixed reaction-container introduction position, and a new reaction container is loaded into the loading unit along with measurement of a previously loaded reaction container without interrupting the measurement.

(2) Second, a method or device for detecting nucleic acid amplification, which uses a loading unit that can load a plurality of reaction containers for nucleic acid amplification, each reaction container containing a sample and a reagent, and has a thermoregulation unit for nucleic acid amplification, and a measurement unit that is disposed facing the loading unit, and measures a reaction in the loaded reaction containers, the measurement unit which is configured to make a repeat of rotational movement or linear movement in a predetermined direction relative to the loading unit to sequentially receive measurement signal from each of the samples in the reaction containers loaded in the loading unit at timing in a fixed period, is characterized in that a temporal range for receiving measurement signals from the reaction containers is set with a sufficient margin to cover across a plurality of specific measurement ranges having different time periods depending on various nucleic-acid amplification conditions, and a measurement-signal receiving period within the temporal range for receiving the measurement signals is set to a period that meets in common various nucleic-acid amplification conditions through control of the relative velocity between the loading unit and the measurement unit, and an appropriate specific measurement range is selected from the temporal range for receiving the measurement signals for each of reaction containers or reaction container groups to be loaded into the loading unit, and a measurement signal contained in the selected specific measurement range is extracted as measurement data for nucleic-acid amplification detection.

Advantage of the Invention

According to the present invention, the configuration (1) enables loading and analysis of a new sample to be randomly added to be performed without interrupting analysis operation (nucleic acid amplification and detection) of a sample (sample) being currently loaded. This eliminates standby time for loading of a sample, leading to speedup of a test. In addition, this enables additional analysis of a sample of an emergency patient, for example, during performance of previous analysis, contributing to an improvement in efficiency of a test.

Furthermore, the configuration (2) achieves concurrent analyses (nucleic-acid amplification detection of samples) of a plurality of samples, which have test items, reagents to be used, temperature programs, and/or other conditions being different from each other, with a common loading unit and a common measurement unit regardless of batch-processed nucleic-acid amplification or randomly-added nucleic-acid amplification.

BRIEF DESCRIPTION OF THE DRAWINGS

FIG. 2-1 is a plan view illustrating a configuration of the nucleic-acid amplification detection device of Example 1.

FIG. 2-2 is a side view of the nucleic-acid amplification detection device of Example 1.

FIG. 2-3 is a side view of a portion A (illustrated in FIG. 2-2) of the nucleic-acid amplification detection device of Example 1.

FIG. 3 is a block diagram illustrating a configuration including a controller and peripheral units thereof used in the nucleic-acid amplification detection device of Example 1.

FIG. 10-1 is a sectional view along B-B' in FIG. 9.

FIG. 10-2 is an enlarged sectional view of a portion C in FIG. 10-1.

MODE FOR CARRYING OUT THE INVENTION

Hereinafter, an embodiment of the present invention will be described with some Examples shown in the accompanying drawings.

Example 1

Figure 1:
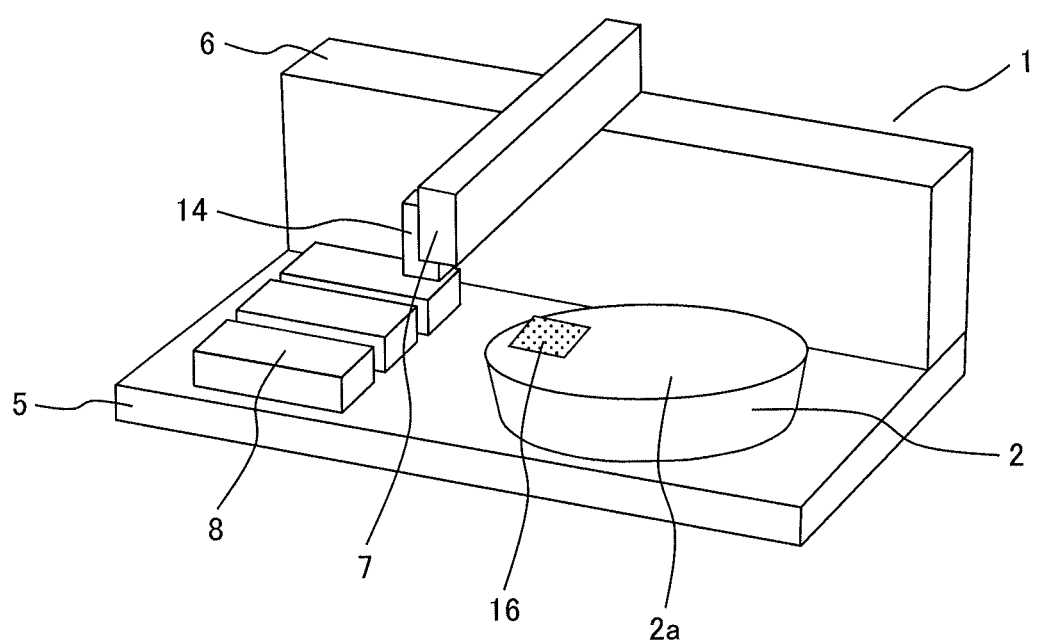
FIG. 1 is a schematic perspective view of a nucleic-acid amplification detection device according to Example 1 of the invention.
Figures 1, 2:
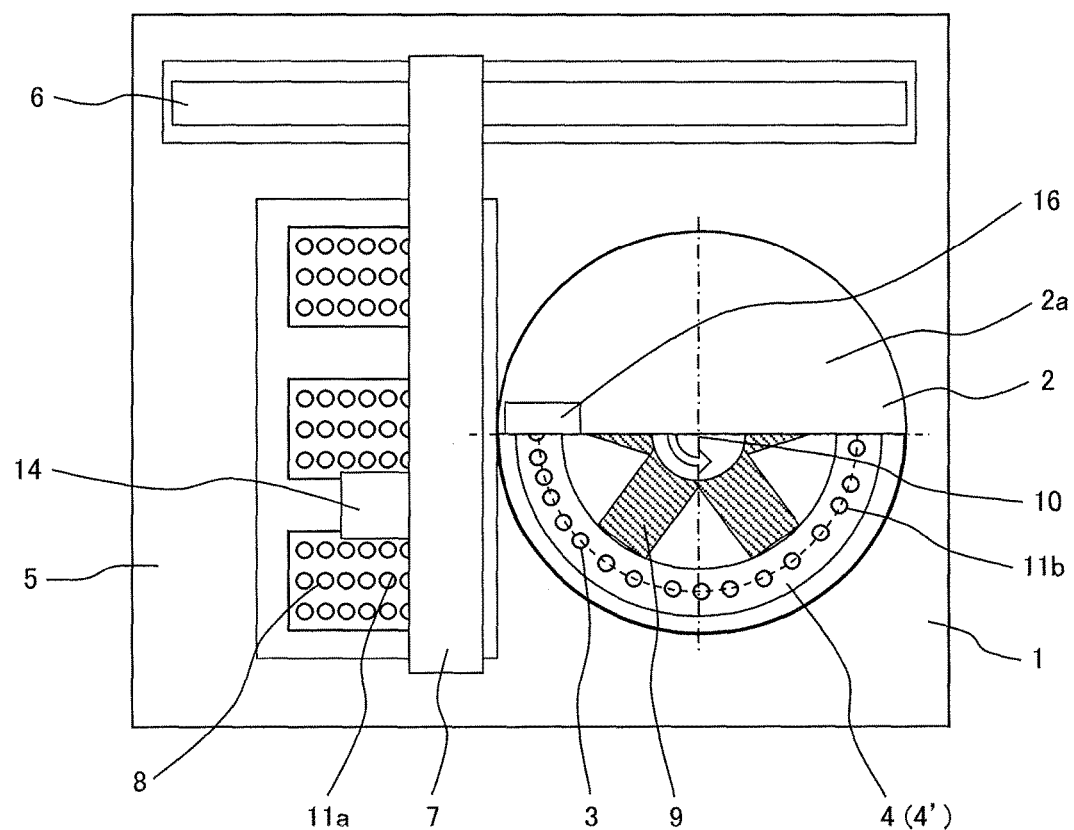
Figure 2:
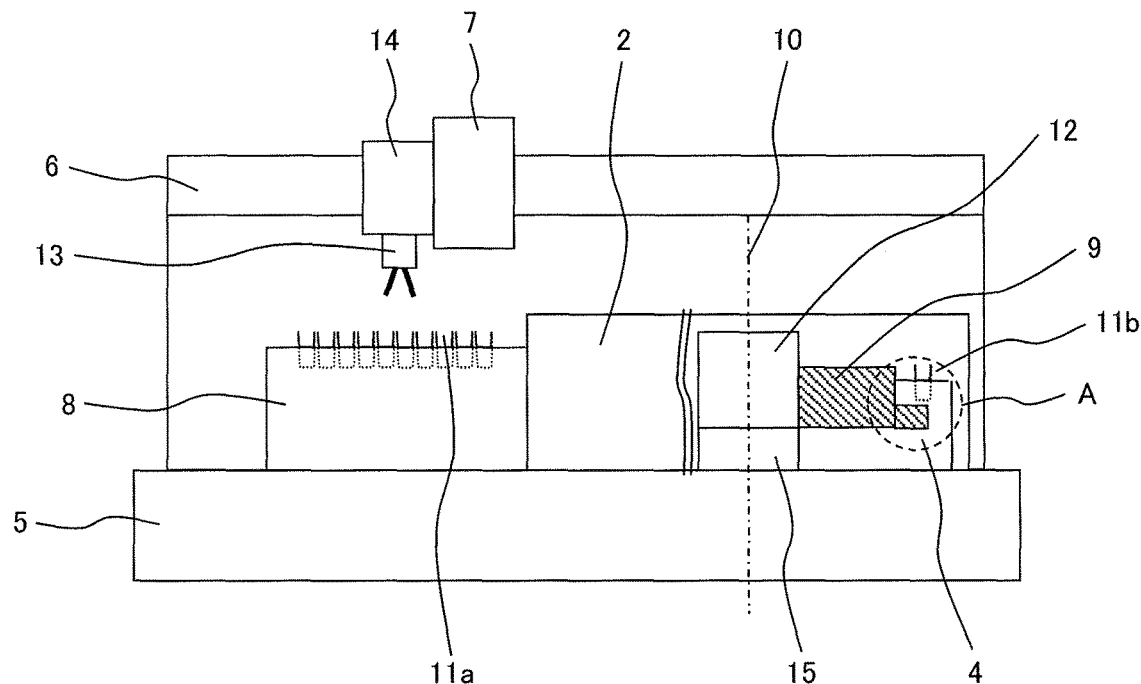
Figures 2, 3:
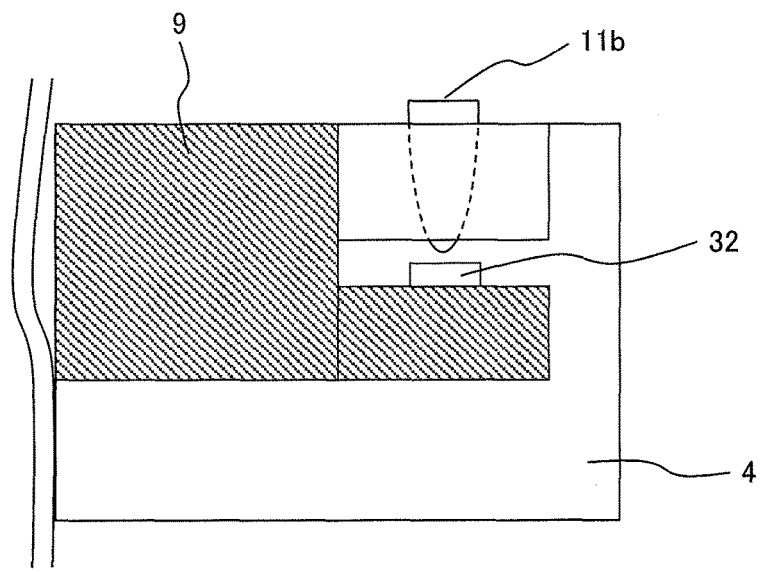
Figure 3:
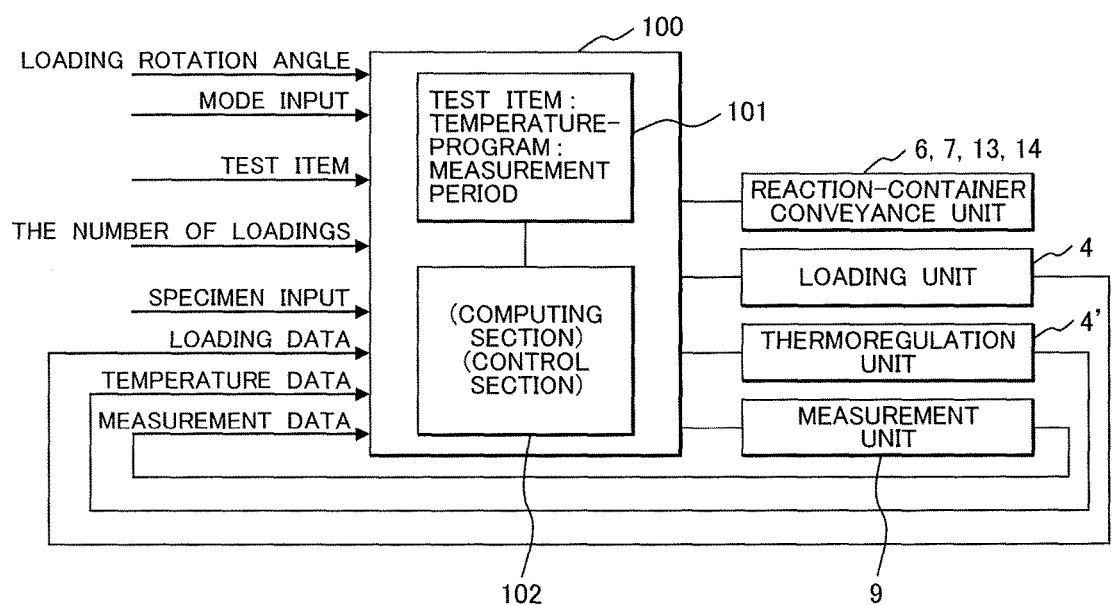

FIG. 1 is a schematic perspective view of a nucleic-acid amplification detection device according to Example 1 of the invention, and FIG. 2-1 is a plan view thereof. For easy understanding of the device, a cover 2a, which entirely covers a loading unit 4 for reaction containers and a measurement unit 9, is partially omitted so that the units 4 and 9 are perspectively illustrated in FIG. 2-1. FIG. 2-2 is a front view of the nucleic-acid amplification detection device according to the Example 1, and FIG. 2-3 is a partial side view thereof.

The nucleic-acid amplification detection device 1 mainly includes a reaction container rack 8 having reaction containers 11a, a reaction container conveyance unit (6, 7, 13, and 14), a loading unit 4 with a thermoregulation unit 4' (FIG. 3), a measurement unit 9 for detection of nucleic acid amplification of a sample (specimen) in each reaction container, and a controller 100 that controls those units. The symbol 11a indicates a reaction container placed in the reaction container rack 8, and a symbol 11b indicates a reaction container placed in the loading unit 4. For convenience, such reaction containers may be collectively referred to as reaction container indicated by a symbol 11.

In the Example 1, the reaction containers 11 are each beforehand filled with a solution containing a sample and a reagent for nucleic acid amplification in a previous process, and are set in the reaction container rack 8 for a plurality of samples. The reaction container rack 8, the reaction container conveyance unit (6, 7, 13, and 14), the loading unit 4 with the thermoregulation unit, and the measurement unit 9 are mounted on a base 5. The controller 100 may be mounted on the base 5, or may be separated from the base 5.

In a main analysis operation, the reaction container 11a containing a sample (specimen) as an object of nucleic-acid amplification detection and a reagent is conveyed from the reaction container rack 8 to the loading unit 4 as a part of a sample testing section 2 (nucleic-acid amplification detection section: the loading unit 4 and the measurement unit 9) with a conveyance unit to be loaded in the loading unit 4, and then the sample in the reaction container is subjected to nucleic acid amplification in the sample testing section 2 with the thermoregulation unit 4' and subjected to nucleic acid amplification detection by the measurement unit 9. Such a series of processes are automatically performed by the controller 100.

The reaction container rack 8 and the sample testing section 2 are adjacently disposed on the base 5 such that the conveyance unit is interposed therebetween.

The sample testing section 2 is comprised of the circular loading unit 4, the measurement unit 9 disposed inside the loading unit facing the loading unit, and the cover 2a covering the loading unit 4 and the measurement unit 9. The top of the cover 2a is provided with a loading gate (a reaction-container receiving position) 16 to receive the reaction container 11, which is sent from the reaction container rack 8 with the conveyance unit, into the loading unit 4. The loading gate 16 is configured to be opened and closed by a shutter. Incidentally, when ambient light has little effect on measurement, or when ambient light is no problem on measurement even if it has effect on measurement, there is no need for the device to be provided with the cover 2a.

The conveyance unit is comprised of an X-axis 6 of the conveyance unit, a Y-axis 7 of the conveyance unit, a Z-axis 14 of the conveyance unit, and a reaction-container grasping mechanism 13 supported by the Z-axis 14. The Z-axis 14 is configured to support the container grasping mechanism 13 so as to be movable in a Z-axis direction (vertical direction), while being supported movably in a Y-axis direction on the Y-axis 7. The Y-axis 7 is supported movably in an X-axis direction by the X-axis 6. Such movement using the X-axis, Y-axis, and Z-axis is performed, for example, by a servo motor (for example, stepping motor) that rotates a ball screw and a servomechanism that converts the rotational motion to linear motion, which is however not illustrated.

The conveyance unit comprising the X-axis 6 of the conveyance unit, the Y-axis 7 of the conveyance unit, the Z-axis 14 of the conveyance unit, and the sample-container grasping mechanism 13, can access all container-placement positions in the reaction container rack 8.

The sample-container grasping mechanism 13 is moved down by the Z-axis 14 of the conveyance unit, catches a reaction container 11a containing a sample from the reaction container rack 8, and moves to a position of the loading unit 4. At that position, the sample-container grasping mechanism 13 places the reaction container in a loading hole 3 of the loading unit 4 through the loading gate 16. The reaction container 11 placed in the loading unit 4 is indicated by the symbol 11b to distinguish it from the reaction container 11a in the reaction container rack 8 as described above.

In the loading unit 4, holes (loading holes) 3 for loading of the reaction container 11 conveyed from the reaction container rack 8 are arranged at equal intervals in a circumferential direction. Each of holes or hole groups is configured to be independently controlled to a given appropriate temperature through thermoregulation for nucleic-acid amplification. For example, a Peltier device, a heater, or a cooling fan is used for the thermoregulation unit 4'. Alternatively, a combination of a heat source for heating and a heat source for cooling may be provided, as long as the combination is structured to allow temperature of each of heating and cooling to be controlled to a given appropriate temperature.

The loading unit 4 is configured to rotate about a central axis 10 in any direction and at any velocity by a stepping motor (not illustrated). The stepping motor is controlled by the controller 100.

The measurement unit 9 is configured to optically measure fluorescence emitted from a nucleic acid labeled by a fluorescent dye, description in detail thereof is omitted because it is a well-known technical matter. The measurement unit 9 is comprised of an excitation light source for fluorescence and a light detector that detects fluorescent emission, one of which is disposed in the inside of the loading unit 4 in a rotatable manner by an actuator such as a stepping motor (not illustrated). The other is fixedly disposed. The measurement unit 9 of the Example 1 has the excitation light source as a movable part and a fluorescence detector 32 (see FIG. 2-3) as a fixed part, and measures fluorescence of the labeling fluorescent dye emitted from a nucleic acid in the reaction container. The fluorescence detector 32 is fixedly disposed for each of the loading holes 3 in such a manner that a measurement signal can be distinguished from other similar detectors. The fluorescence may be measured in any other manner, for example, may be measured through a side face of the container. Here, the excitation light source as the movable part is illustrated as the measurement unit 9.

The number of excitation light sources placed in the measurement unit 9 since varies depending on the number of fluorescent dyes to be detected, one or more excitation light sources may be placed. When two or more excitation light sources are provided, they act as the measurement unit 9 as the movable part, and are used as common light sources for the fluorescence detectors 32 provided on the lower sides of the loading holes 3, and rotate together. The measurement unit 9 is also configured to rotate about the central axis 10 in any direction and at any velocity. The thermoregulation unit 4 and the measurement unit 9 are configured to be independently rotated by their respective drive mechanisms (for example, stepping motors) in the same direction or opposite directions. Note that the fluorescence detector part may be disposed as a movable part, while the excitation light source part as a fixed part.

A positional relationship between the measurement unit (movable part) 9 and the loading unit 4 (thermoregulation unit 4') may include a layout where the measurement unit 9 is disposed outside the loading unit 4. The measurement unit 9 and the loading unit 4 may each have any shape and/or structure as long as relative velocity between the measurement unit 9 and the thermoregulation unit 4 (reaction container 11b) is maintained constant during nucleic-acid amplification detection.

The controller 100 illustrated in FIG. 3 controls drive of each of the conveyance unit (6, 7, 13, and 14), the loading unit 4, the thermoregulation unit 4', and a driver (servo actuator) of the measurement unit 9. Such control is described with reference to a flowchart of FIG. 4 and a time chart of FIG. 5.

The controller 100 defines, as a normal mode (mode 1), a case where one or more (a batch of) reaction containers are loaded to start nucleic-acid amplification detection in an initial state where reaction containers are still not loaded into the loading unit 4, and defines, as an interrupt mode (mode 2), a case where an additional reaction container is loaded for nucleic-acid amplification detection while a previously loaded reaction container is being subjected to nucleic-acid amplification detection, and selects one of the modes.

When initial test items and the number of loading requests (the number of sample requests) are received (step S1), the model is selected (step S2), and the loading unit 4 is controlled to be intermittently moved so that empty loading holes 3 are sequentially moved to a position directly below the loading gate 16 in order of closeness to the loading gate 16. The reaction containers 11 (11a) are sequentially loaded from the reaction container rack 8 into such sequentially fed holes 3. In this operation, the loading unit 4 is controlled at a constant intermittent rate.

Regarding positions of the loading holes (holder positions) 3, a leading hole as a reference is at a given position directly below the loading gate 16 in the initial state, which may be hereinafter referred to as an loading gate position. Each of the holes 3 arranged on the loading unit 4 can be recognized with a relative angle (distance) between the leading hole as the reference and each own hole by means of a rotation angle detector (not illustrated) such as an encoder. The rotation angle detector constantly measures a rotation angle (moving distance) of the loading unit 4 from the initial position during rotation of the loading unit 4.

The angle (distance) $\alpha$ between any loading hole 3 and the loading gate 16 is obtained from $\alpha=A+B$, where A represents a rotation angle from the position of the leading hole (reference hole) to the loading gate position, and B represents a relative angle from the leading hole to the any loading hole.

Each reaction container 11 is marked with an identification code for a sample. The identification code is received at loading of the reaction container 11 in the loading unit 4 (as sample input), and which sample (reaction container) is loaded in a certain number loading hole from the reference hole (leading hole) is understood based on the information of the identification code and the angle $\alpha$. As a result, an computing/control section 102 also understands empty information of the loading holes.

When the reaction container is loaded, the controller 100 immediately starts individual thermoregulation operation for a relevant loading hole with the thermoregulation unit 4' according to the identification code of a sample and the test item information (step S4). Consequently, the thermoregulation can be performed without waiting for loading of other reaction containers, resulting in elimination of standby time for start of nucleic acid amplification. In the thermoregulation of each loading hole 3 for each test item, when PCR is performed, the thermoregulation is differently performed at every stage with a temperature cycle control, and when nucleic acid sequence-based amplification is performed, the thermoregulation is performed with a constant temperature control.

In the mode 1, the loading unit 4 is intermittently moved to load reaction containers, and therefore frequently repeats brief rotation and brief stop. In order to simplify control of the loading unit and the measurement, after loading a batch of reaction containers, intermittent rotation of the loading unit 4 is stopped, and rotation of the measurement unit 9 is then controlled (steps S5 and S6).

In step S6, the measurement unit 9 is subjected to such rotation control (constant velocity control), and measurement signals are received from the reaction containers 11b loaded in the loading unit 4.

The measurement unit 9 is controlled at a constant relative velocity (angular velocity) with respect to the loading unit 4 (in other words, the loaded reaction container 11b). In other words, rotation of the measurement unit 9 itself is controlled at a setting velocity V while the loading unit 4 is being stopped (loading has been completed). Such a constant relative velocity V is maintained, so that the measurement period P for each reaction container 11b on the loading unit 4 is given as $P=\pi r^2/V$, where r represents the radius of the loading unit 4. The measurement signals (measurement data) from the reaction containers 11b are sequentially input to the computing/control section 102 of the controller 100 in the period P.

The measurement signals are repeatedly received in the predetermined period P for individual reaction containers during execution of a temperature cycle along a temperature program of nucleic acid amplification. The measurement data used for nucleic-acid amplification detection may not be obtained from any measurement signal in any time period of the temperature cycle. Specifically, a reagent, temperature cycle time, and/or cycle number each vary depending on test items (nucleic-acid amplification condition) to be executed; hence, a specific measurement range in the relevant temperature cycle also varies depending on the test items. A time period (temporal specific-range), in which nucleic acid amplification is detected, is specified or recommended by a reagent manufacturer depending on protocols of quantitative examination.

Figure 11:
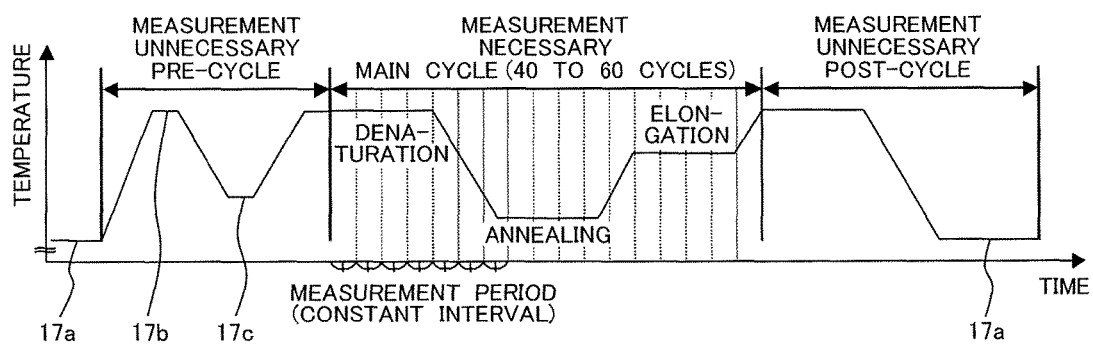
FIG. 11 is a schematic illustration of an exemplary temperature program (temperature cycle) of nucleic acid amplification with PCR.
Figure 12:
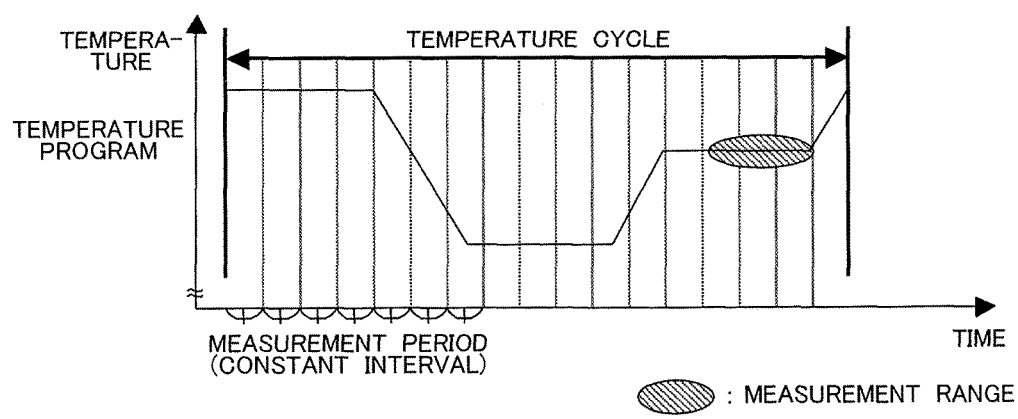
FIG. 12 is a schematic illustration of part of the temperature program (temperature cycle) of FIG. 11.

For example, as illustrated in FIG. 11, in quantitative examination with PCR, while a main cycle, in which measurement is necessary, includes denaturation, annealing, and elongation of a nucleic-acid amplification step, signals in the range (time period) of the elongation must be used particularly for nucleic-acid amplification detection. Thus, in the Example 1, the measurement signals are received with a sufficient margin (at constant intervals) during the period of the main cycle, and as illustrated in FIG. 12, a time period (a hatching portion of FIG. 12) corresponding to the elongation is determined as a specific measurement range for nucleic-acid amplification detection, so that measurement signals in the specific measurement range are used as the data for nucleic-acid amplification detection (step S7).

Figure 13:
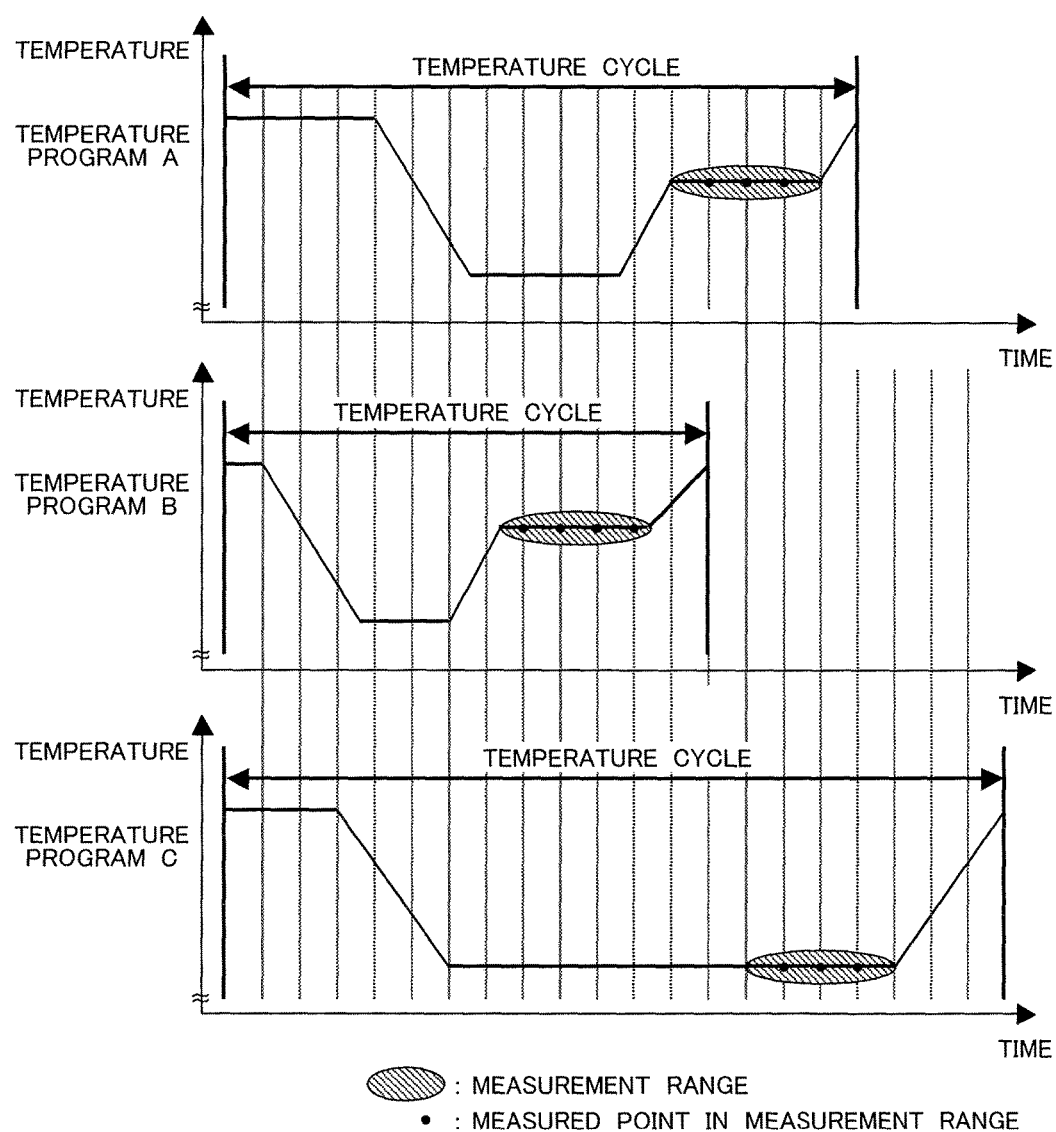
FIG. 13 is a schematic illustration of a state where measurement signals are captured in a common period with a common measurement unit in nucleic acid amplification performed according to different temperature programs (temperature cycles).

As illustrated in FIG. 13, in the Example 1, under condition that a batch of samples (samples in the reaction containers) is loaded into the loading unit 4, i.e., even when a temperature program varies for each of the batch of samples (namely, a temperature cycle varies for each of the samples), and even when the specific measurement range correspondingly varies for each sample, the device is configured to perform parallel processing for nucleic acid amplification of the samples and detection of the nucleic acid amplification. FIG. 13 includes time charts illustrating the principle of parallel processing of nucleic-acid amplification detection for all samples even when a time period (timing) for detection varies depending on samples in the above way. FIG. 13 illustrates, as an example, a relationship between a temperature program and a measurement period in PCR executed for each of three samples (reaction containers 11*b*) having different test items. As illustrated in FIG. 13, the samples have different temperature programs (temperature cycles), and accordingly have different specific measurement ranges required for the test, the measurement ranges being marked with hatching. In the Example 1, a temporal range for receiving measurement signals from the reaction containers is established to meet a temperature cycle (the longest temperature cycle) in the bottom of FIG. 13. The temporal range for receiving the measurement signals is set with a sufficient margin to cover all the required, specific measurement ranges (hatched three ranges illustrated in FIG. 13). In FIG. 13, while vertical thin lines are drawn at equal intervals in the temperature cycle, a space between the lines indicates a generation period (receiving period) P of a measurement signal extracted when the measurement unit 9 just reaches one of the reaction containers 11*b*. The measurement signals from the three samples in FIG. 13 are sequentially extracted along with rotation of the measurement unit, and therefore the periods of the measurement signals actually have time differences therebetween. The periods, however, have a common length.

A storage device 101 of the controller in FIG. 3 beforehand stores a temperature program, and the specific measurement range and the period P as illustrated in FIG. 13 for each of test items as nucleic-acid amplification conditions corresponding to the various test items. When the controller 100 receives a test item, the controller 100 performs thermoregulation for nucleic acid amplification based on the corresponding temperature program and specific measurement range, extracts the measurement signal in the specific measurement range, and uses the extracted measurement signal as data for nucleic-acid amplification detection.

In the Example 1, even when a plurality of samples have measurement ranges (specific measurement ranges) that are different depending on various test items (conditions of nucleic-acid amplification detection), signals in each specific measurement range are extracted as test data in a common measurement period with the common measurement unit 9. Consequently, a plurality of nucleic-acid amplification detection steps with different temperature programs can be performed in parallel.

When the temperature cycle is completed, the reaction containers are ejected (steps S8 and S9).

When a randomly added reaction container is loaded, and when nucleic acid amplification and detection for the reaction container are requested during performance of such nucleic acid amplification and detection in the normal mode (mode 1) (step S10), the mode is shifted to the mode 2 (step S11). When the mode 2 is executed, an interrupt loading process shown by the following steps S12 to S14 is executed under control of the controller 100 so as not to interrupt the nucleic acid amplification and reception of the measurement signals in a setting period P for the previously loaded reaction containers in the mode 1. The mode 2 may be executed by either PCR or nucleic acid sequence-based amplification.

The reason why the mode 2 must be executed is described before description of the mode 2.

In the case where one or more additional reaction container is singly or in series loaded in the testing section (the loading unit 4 and the measurement unit 9) in an interruptive manner, and when test items are different between a sample being subjected to a previous nucleic-acid amplification detection step and the newly added sample, the temperature cycle and/or the detection time period (detection timing) are different from each other depending on the test items. In this way, when the number of samples having different test items and being concurrently tested, is further increased, all the time periods for detection (specific measurement ranges) may be different from each other.

In addition, as long as the device has a function of continuous loading in an interruptive manner, it is probable that samples are introduced into/ejected from the loading unit 4 in parallel. Specifically, measurement operation must be continuously performed during continuous loading of samples.

Provided that the thermoregulation unit 4' and the detection unit are each independently provided for each of the samples to be analyzed, it is possible to lead to relatively easy control for the continuous measurement operation concurrent with introduction/ejection of the reaction containers into/from the loading unit 4. In such a case, an optical system and/or a loading unit to be configured, preferably should be shared as much as possible to reduce the number of components in light of variations in data between the samples, adjustment operation of each mechanism to prevent the variations, device cost, and/or other factors.

Figure 5:
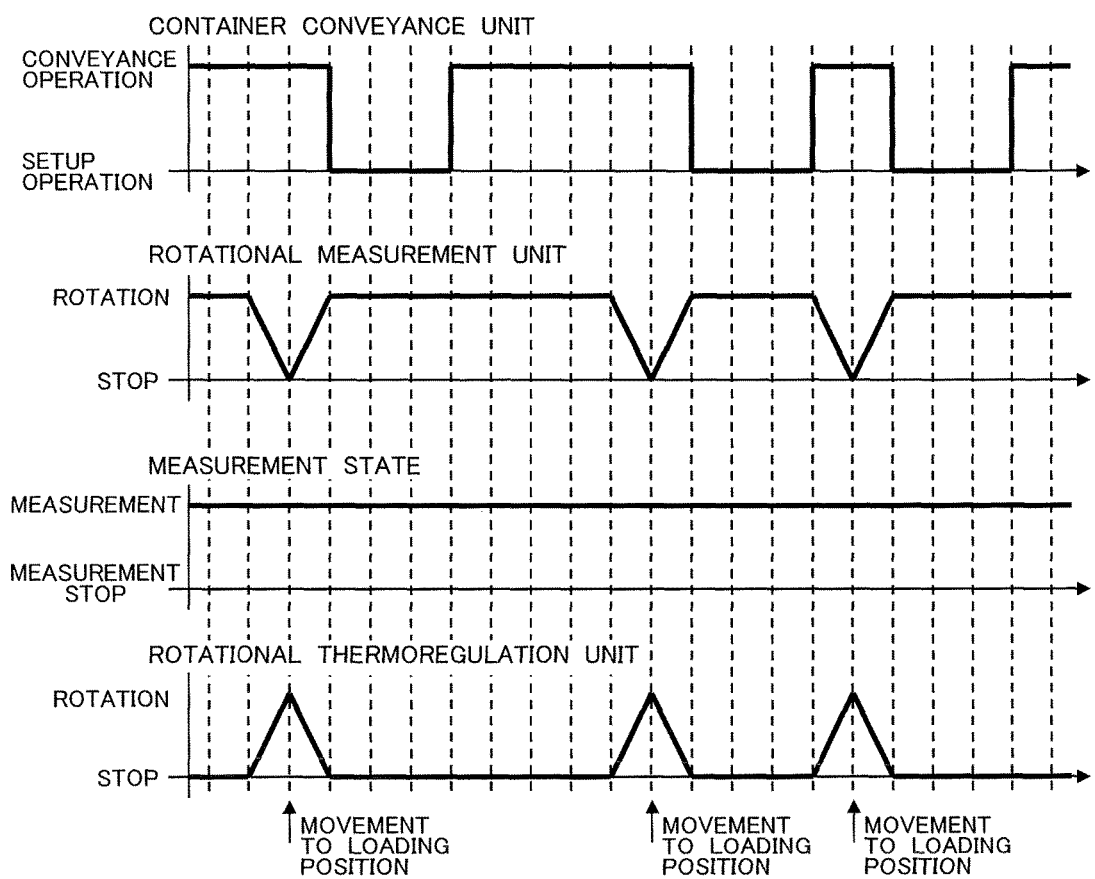
FIG. 5 is a time chart illustrating operation of the nucleic-acid amplification detection in Example 1.

In the Example 1, in the nucleic-acid amplification detection device of a batch processing type such as the mode 1, a common component is used for a plurality of samples, for example, in the optical system, and the mode 2 is selected to allow additional analysis of a new sample to be conducted without interrupting a process of previous analysis that has been conducted. Therefore, the following operation is executed. In this case, although nucleic-acid amplification detection may be executed by either PCR or nucleic acid sequence-based amplification, description is made with PCR in the Example 1. FIG. 5 illustrates a time chart used in the Example 1.

Figure 4:
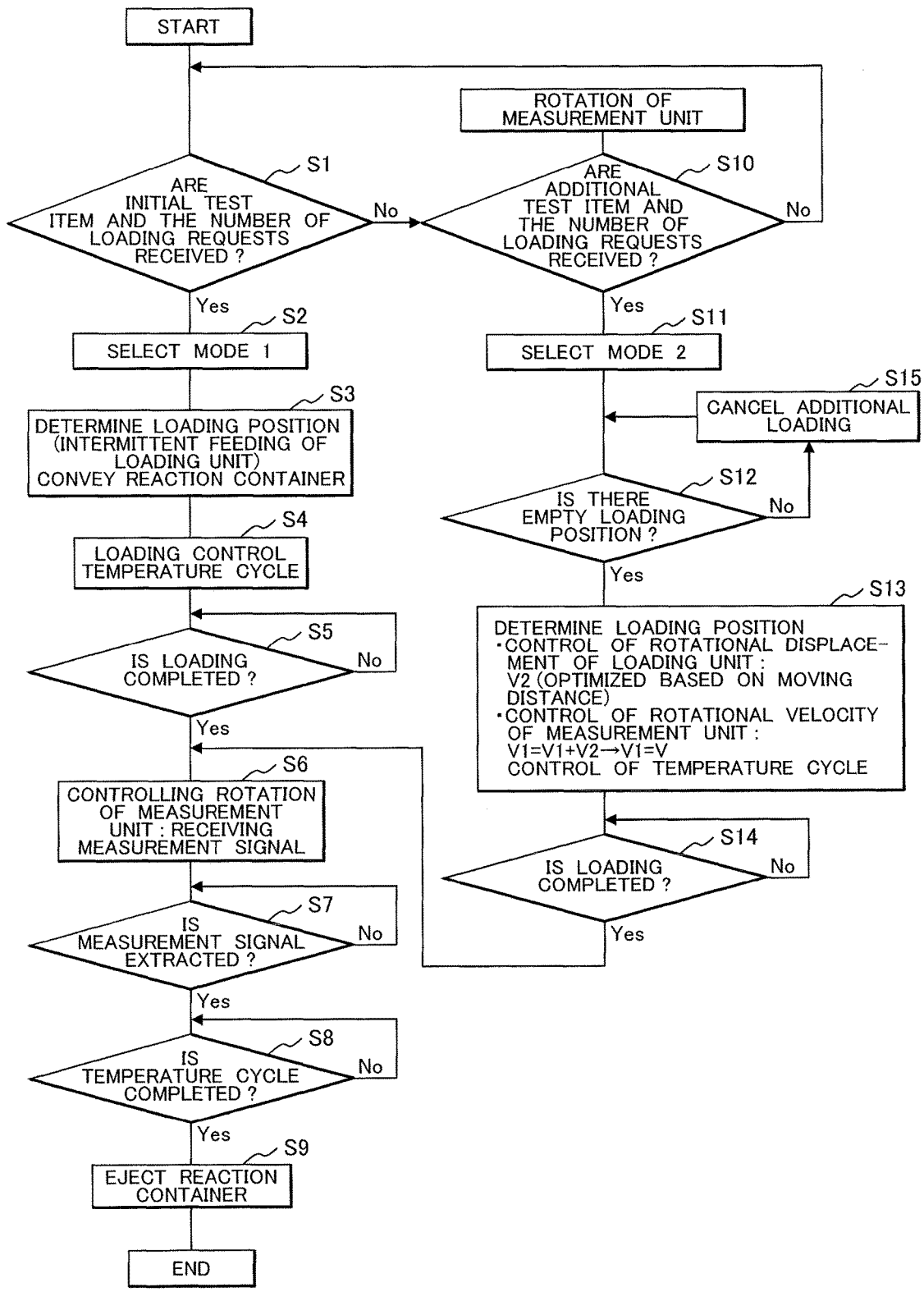
FIG. 4 is a flowchart illustrating operation of nucleic-acid amplification detection in Example 1.

As illustrated in FIG. 4, when test items and the number of loading requests of an additional sample are received during nucleic-acid amplification detection (during rotation of the measurement unit (step S12), the mode is shifted to the mode 2 (step S11), and an empty state of each loading hole 3 of the loading unit 4 is checked (step S12). The empty state of the loading hole 3 can be determined through constant update and storage of a loaded state of a reaction container in each loading hole based on an operation history of the device (a history of rotational displacement of the loading unit and a loading history of each reaction container), for example. When an empty hole exists, the computing/control section 102 of the controller calculates a relative distance α between the empty hole 3 and the loading position at which the loading gate 16 is located. The relative distance is obtained from α=A+B, where A represents a rotation angle from the position of the above-described leading hole as a reference to the introduction position, and B represents a relative angle from the leading hole (reference hole) to any one of other (empty) holes. When no empty hole exists, the additional loading is cancelled (step S15). When some empty holes 3 exist, a hole nearest the loading gate 16 is selected among the empty holes 3 (step S13: loading position determination).

In addition, a movement direction and movement velocity (angular velocity) of the loading unit 4 are determined such that the selected empty hole is rotationally displaced to the position of the loading gate 16 in a shortest time.

In the Example 1, the measurement period P must be maintained constant as described above; hence, the computing/control section 102 performs the following velocity calculation to constantly maintain the relative angular velocity V between the loading unit 4 (a reaction container 11$b$ being measured) and the measurement unit 9 to be constant (step S13).

The angular velocity of the measurement unit 9 is defined as V1, and the angular velocity of the loading unit 4 (thermoregulation unit 4') is defined as V2. The values of V1 and V2 are determined such that the V is maintained constant. The determined values are used for movement of the measurement unit and the loading unit. When the loading position (empty hole) 3 selected by the loading unit 4 is rotationally displaced to the loading gate position, the angular velocity V1 of the measurement unit 9 is defined by formula (1).

$$V1=V+V2 \qquad (1)$$

Here, the target relative angular velocity V is known, and the optimum value of the angular velocity V2 of the loading unit 4 is determined based on the movement distance from the selected empty hole 3 to the loading gate 16, a rotation direction, and a motor specification, and then V1 is calculated based on the obtained V and V2. V2 is set to be higher as the movement distance increases. Among the positions of the holes 3, a position most away from the loading gate 16 corresponds to a position 180° rotated from the position of the loading gate 16. Therefore, when a selected hole 3 is rotated to the position of the loading gate 16 in the shortest distance, the rotation direction of the loading unit 4 must be switched between a normal or reverse direction in accordance with (a) a case of 0°<position of hole 3≤180° or (b) a case of 180°<position of hole 3<360° with respect to the loading gate 16.

During rotation operation of the loading unit 4, a velocity state includes velocity patterns of acceleration, fixed velocity, and deceleration. Depending on the velocity, the fixed velocity state does not occur in a short movement distance. In contrast, more time is taken before finish of the rotation in a long movement distance. Thus, the computing/control section 102 determines the movement velocity (rotation velocity) of the loading unit 4 depending on the angle (distance) at the time of loading. The rotation velocity (angular velocity) of the measurement unit 9 is also determined such that the relative velocity V is maintained constant, and is controlled by the computing/control section 102.

When no interruptive loading operation is executed (mode 1), namely, when only the measurement unit 9 moves, the angular velocity of each of the both units is represented as formula (2).

$$V1=V, V2=0 \qquad (2)$$

The angular velocity of each of the loading unit 4 and the measurement unit 9 is determined by formulas (1) and (2), along with which rotation of each of the both units is controlled.

After the selected empty hole 3 of the loading unit 4 comes to the position of the loading gate 16, the reaction container is loaded into the empty hole 3 with the conveyance unit and through the loading gate 16.

FIG. 5 illustrates an operation for maintaining the relative velocity V between rotation of the rotational measurement unit 9 and that of the rotational loading unit (thermoregulation unit) 4, in relation to conveyance operation of the container conveyance unit. FIG. 5 illustrates a state where the measurement unit rotates at a fixed velocity as the relative velocity while making a stop of the loading unit (thermoregulation unit), and a state where, while the empty hole of the loading unit (thermoregulation unit) is moved to the reaction-container loading gate 16, velocity control is performed such that the measurement unit maintains the relative velocity in response to rotation of the loading unit.

In step S13, when the reaction container is loaded, individual thermoregulation operation is immediately started at the loading position and then continued until the end of a thermoregulation process including a series of temperature cycles. When the additional loading is completed (step S14), the state expressed by formula (2) is kept, and only the measurement unit 9 rotates until a new additional loading request (additional request of nucleic-acid amplification detection) is received (step S6). Thereafter, the above-described steps S7 to S9 are performed. When an additional request is received halfway, the mode is shifted to the mode 2, and a series of operation steps beginning with check of an empty loading hole are repeated. A measurement signal is extracted in step S7 in accordance with the above-described principle as shown in FIG. 13.

Specifically, the temporal range for receiving measurement signals from the reaction containers is set with a sufficient margin to cover across a plurality of specific measurement ranges having different time periods depending on various nucleic-acid amplification conditions. A measurement-signal receiving period within the temporal range for receiving the measurement signals is set to a period that meets various nucleic-acid amplification conditions through control of the relative velocity between the loading unit (thermoregulation unit) 4 and the measurement unit 9. The controller 100 selects an appropriate specific measurement range for each of reaction containers or reaction container groups to be loaded, and extracts a measurement signal contained in the selected specific measurement range as measurement data for nucleic-acid amplification detection.

The above operation enables continuous loading of reaction containers concurrent with constant measurement regardless of presence of addition (interrupt) of loading.

Although FIG. 5 illustrates an exemplary case of three additional samples (reaction containers), a fourth or higher reaction container can be also successively loaded into a loading hole independently of the measurement unit until all empty loading holes are loaded with the reaction containers. When the amplification process has been finished, the loaded reaction container may be ejected by means of either the conveyance unit or an additional mechanism that drops the reaction container from a setup hole at an ejection point.

Although the relative velocity between the measurement unit and the loading unit is set based on the shortest time for fluorescent measurement performed during passage of the measurement unit along each reaction container, the relative velocity may be appropriately set depending on measurement time. While the loading holes for the reaction containers are provided in the thermoregulation unit, the measurement unit passes along one of the loading holes at timing in a fixed period. Consequently, while the measurement unit performs measurement of nucleic-acid amplification detection of samples in an appropriate measurement period, the reaction containers can be continuously loaded.

The above-mentioned loading and measurement for reaction containers may be performed in any of test method combinations for a sample being currently analyzed and an added sample, including a combination of PCR and PCR, a combination of nucleic acid sequence-based amplification and nucleic acid sequence-based amplification, and a combination of PCR and nucleic acid sequence-based amplification.

Furthermore, this system allows determination of the loading position of the reaction container at any one point (or two or more points). As a result, a distance of conveyance by the conveyance unit can be set to the shortest distance, and consequently conveyance operation can be performed in the shortest time. In addition, a position of the conveyance unit can be calibrated with few positions to be specified. In addition, when a cover is provided, only one loading gate should be provided.

When the relative angular velocity V is constant, the measurement condition, such as velocity and/or time of movement of the measurement unit along the container, can be equalized for a plurality of containers, leading to a reduction invariance in measurement between containers due to variations of data acquisition conditions. In other words, operation of the loading unit would not prevent the measurement under a constant condition. Thus, although the measurement unit and the thermoregulation unit each have a circular shape in the Example 1, each mechanism may have any other shape as long as a plurality of samples can be sequentially measured by the measurement unit and the thermoregulation unit arranged so as to face each other.

Since the loaded position of each reaction container is known, the necessity of the measured data can be determined from a measured time, so that data necessary for the loading position of the reaction container to be measured can be put together in time sequence. Note that such a method for data collection is not limitative, and all or any required number of data may be collected as necessary.

Example 2

Although a method of detecting nucleic acid amplification with PCR has been exemplified in the Example 1, the loading unit 4 may have a thermoregulation unit performing nucleic acid sequence-based amplification. The amplification process in the nucleic acid sequence-based amplification is performed at a fixed temperature; hence, functions of the thermoregulation unit can be simplified. Specifically, the reaction-container setup holes in the thermoregulation unit as described in the Example 1 may be collectively subjected to thermoregulation instead of individual thermoregulation. In this case, for example, a Peltier device, a heater, or a cooling fan is used for thermoregulation. Alternatively, a combination of a heat source for heating and a heat source for cooling may be provided, as long as the combination is structured to allow temperature of each of heating and cooling to be adjusted to any appropriate temperature. Other configurations are similar to those in Example 1.

Example 3

In the Example 1, the loading unit 4 has one fixed reaction-container loading position, and the loading unit 4 is controlled to be moved such that an empty loading hole 3 reaches the reaction container loading position. In contrary, in Example 3, while the loading unit is fixed, the measurement unit has a movement mechanism with which relative velocity between the measurement unit and the loading unit is maintained constant. The Example 3 is achieved through the following modification (not illustrated) of the Example 1 illustrated in FIGS. 1 to 2-3.

Specifically, while the loading unit 4 is fixed, the measurement unit 9 is rotatable. When a reaction container is loaded into a selected empty loading hole, the conveyance unit (6, 7, 13, and 14) selects a nearest empty hole 3, and the reaction container 11 is conveyed from the reaction container rack 8 to the position of the selected empty hole 3 with the conveyance unit.

When the cover 2a is provided, a position corresponding to the loading hole 3 may be opened or closed by a shutter. Alternatively, a cover for the entire device may be provided in place of the cover 2a for only a testing section so that the cover blocks outside light and/or stray light.

As in the Example 1, a temporal range for receiving measurement signals, a measurement period, and a specific measurement range are set as illustrated in FIG. 13.

Figure 6:
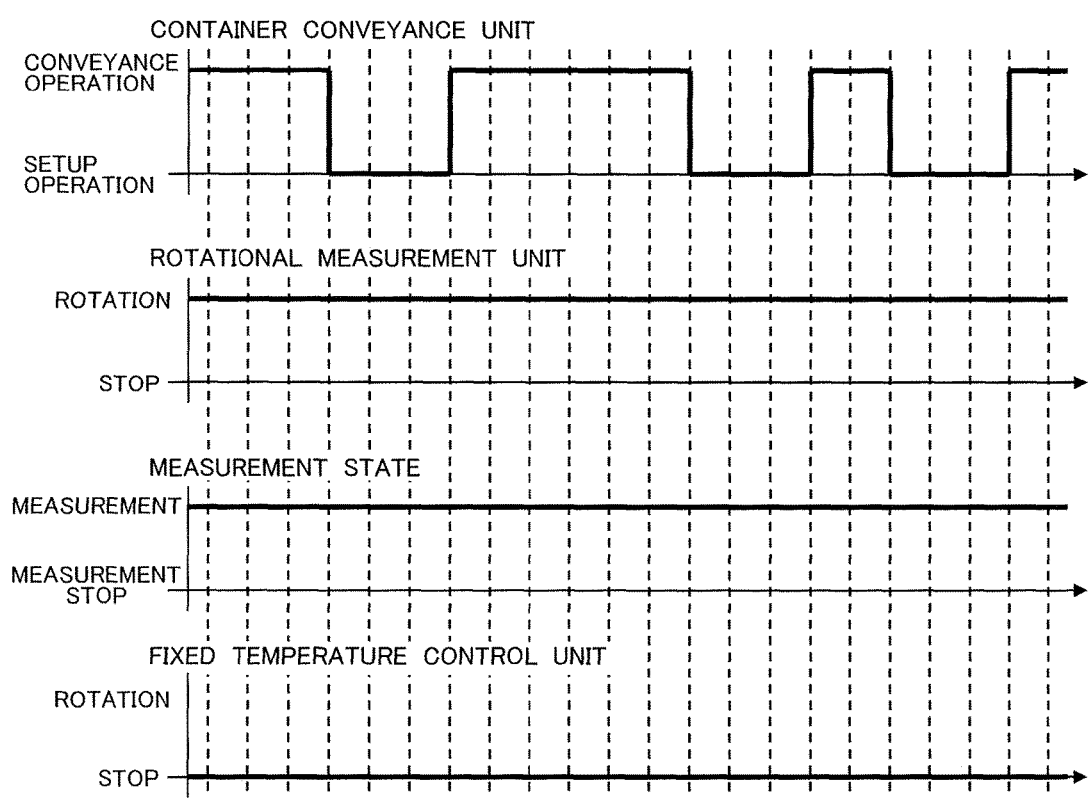
FIG. 6 is a time chart illustrating operation of nucleic-acid amplification detection in Example 3 of the invention.

FIG. 6 illustrates a time chart of each of the conveyance unit, the loading unit (thermoregulation unit), and the measurement unit used in the Example 3.

As illustrated in FIG. 5, in the Example 3, the relative velocity V between the measurement unit 9 and the loading unit (thermoregulation unit) 4 is also maintained constant, so that measurement signals for nucleic-acid amplification detection can be received in a fixed measurement period P, and measurement signals can be extracted in parallel from a plurality of samples having different nucleic-acid amplification conditions (specific measurement ranges). Moreover, even when loading and nucleic-acid amplification detection of an additional sample are requested, the reaction container can be loaded into a selected, fixed empty hole with a conveyance unit while the relative velocity V is maintained in each case of PCR having different temperature programs and nucleic acid sequence-based amplification.

According to the Example 3, movement velocity (angular velocity) of the measurement unit 9 is also kept to the velocity V during loading of a reaction container, and the same advantageous effects as in the Example 1 illustrated in FIG. 1 are achieved while control of velocity of the measurement unit is simplified during the nucleic-acid amplification detection process.

Example 4

Figure 7:
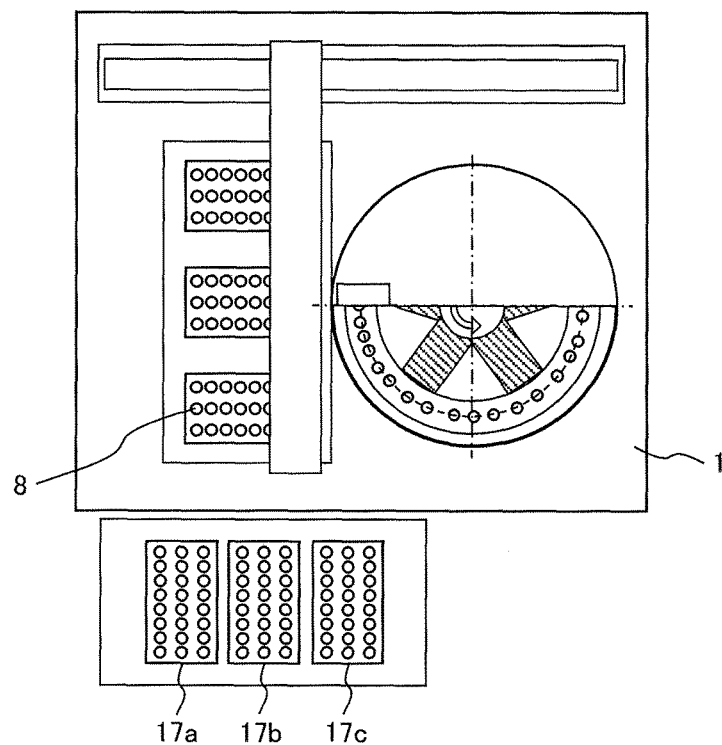
FIG. 7 is a plan view illustrating a configuration of a nucleic-acid amplification detection device of Example 4 of the invention.

In a method of Example 4, only a part of the temperature cycle necessary for PCR is performed in a nucleic-acid amplification device having a configuration similar to that of the Example 1. FIG. 7 illustrates the configuration of the nucleic-acid amplification device of the Example 4.

In PCR, as illustrated in FIG. 11, the temperature cycle may be divided into a pre cycle, a main cycle, and a post cycle depending on protocols. Among them, a signal needs to be acquired from a fluorescent dye only in the main and post cycles. In the Example 4, only temperature cycles necessary for measurement are performed in the nucleic-acid amplification device 1 of the invention, and other temperature cycles are performed in individual temperature controller 17 (17a, 17b, and 17c) outside the device 1. Here, a reaction container containing a sample is conveyed in order of the individual temperature controller 17, the nucleic-acid amplification device 1, and the individual temperature controller 17.

In this way, the function of performing a temperature cycle is finely separated from each other, thereby the degree of freedom of operation of the nucleic-acid amplification device 1 can be increased.

Example 5

Figure 8:
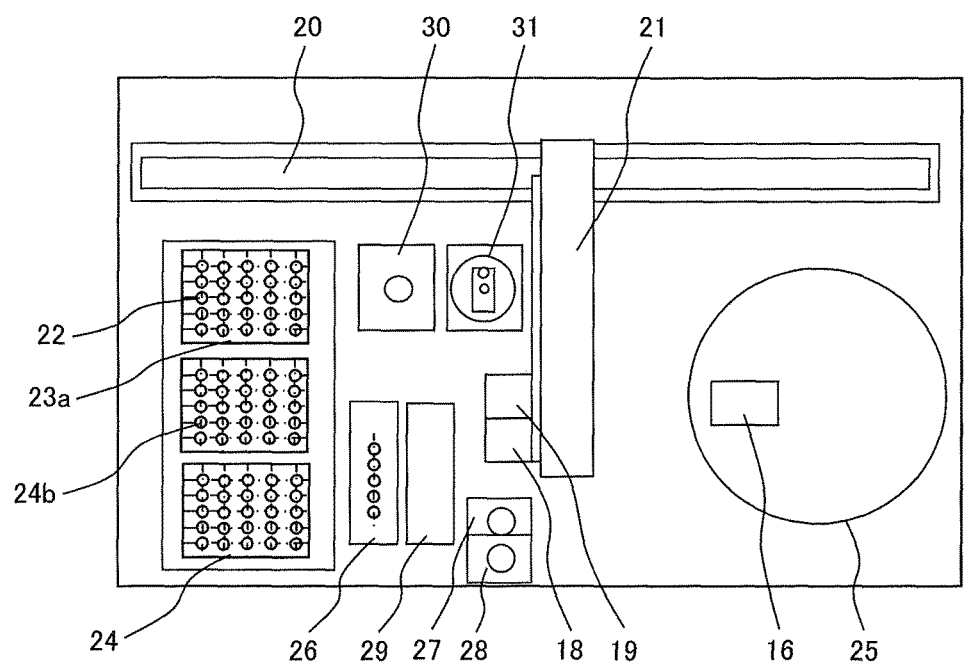
FIG. 8 is a plan view illustrating a configuration of a nucleic-acid amplification detection device of Example 5 of the invention.

FIG. 8 is a plan view of a nucleic-acid amplification detection device (an automatic analyzer) according to Example 8 of the invention.

In the Example 5, the basic configurations relevant to the invention of the conveyance unit, the loading unit with the thermoregulation unit, and the measurement unit are also similar to those in Example 1.

The Example 5 is different from Example 1 in the following points.

In the Example 5, the nucleic-acid amplification device itself includes a pipetting unit 18 and a gripper unit 19. The pipetting unit 18 performs aspiration and dispensing of a liquid. The gripper unit 19 grasps a reaction container 32. The pipetting unit 18 and the gripper unit 19 are each connected to an X-axis 20 of a robot arm and a Y-axis 21 of the robot arm so that the units 18 and 19 can move in a plane.

A chip rack 23a stocks pipetting chips 22. A reagent container rack 23b stocks reagent containers each of which contains a reagent. A reaction container rack 24 stocks reaction containers each of which contains a sample. A nucleic-acid amplification detection section 25 has a fluorescent detector for tracing an amplification process of nucleic acid in time sequence.

A typical operation example of the automatic analyzer of the Example 5 is now described. A reaction container is conveyed to a reaction-solution preparation position 26 by the gripper unit. A pipetting chip 22 is loaded in the pipetting unit 18 to aspirate a reagent from the reagent container containing the reagent and dispense the reagent into a reaction container at the reaction-solution preparation position. The used pipetting chip is disposed into a disposal box 29 to prevent contamination. The reaction container containing a sample and the reagent is conveyed to a capping unit 30 by the robot arm while being grasped by the gripper unit 19. The reaction container is then closed with a cap in the closing unit 30, and is then conveyed to an agitation unit 31 by the robot arm. The content of the conveyed reaction container is agitated, and the reaction container is then conveyed to the nucleic-acid amplification detection section by the robot arm for amplification and detection as in Example 1. After the detection, the reaction container is disposed into the disposal box. The reaction container is carried into/out of the nucleic-acid amplification detection section 25 through the loading gate 16 being opened.

According to the invention of the Example 5, a quantitative determination process of nucleic acid with nucleic acid amplification can be automated. Although the pipetting unit and the gripper unit are connected to the set of robot arms in the Example 5, any configuration of the conveyance unit may be used, for example, the respective units may be connected to independent robot arms, or the units may be connected to a rotational arm with a fixed axis. In addition, although automation is started from the pretreatment step prior to the amplification step, such as reagent preparation, in the Example 5, for example, all steps including the nucleic-acid extraction step may be automated without limitation.

Example 6

Figure 9:
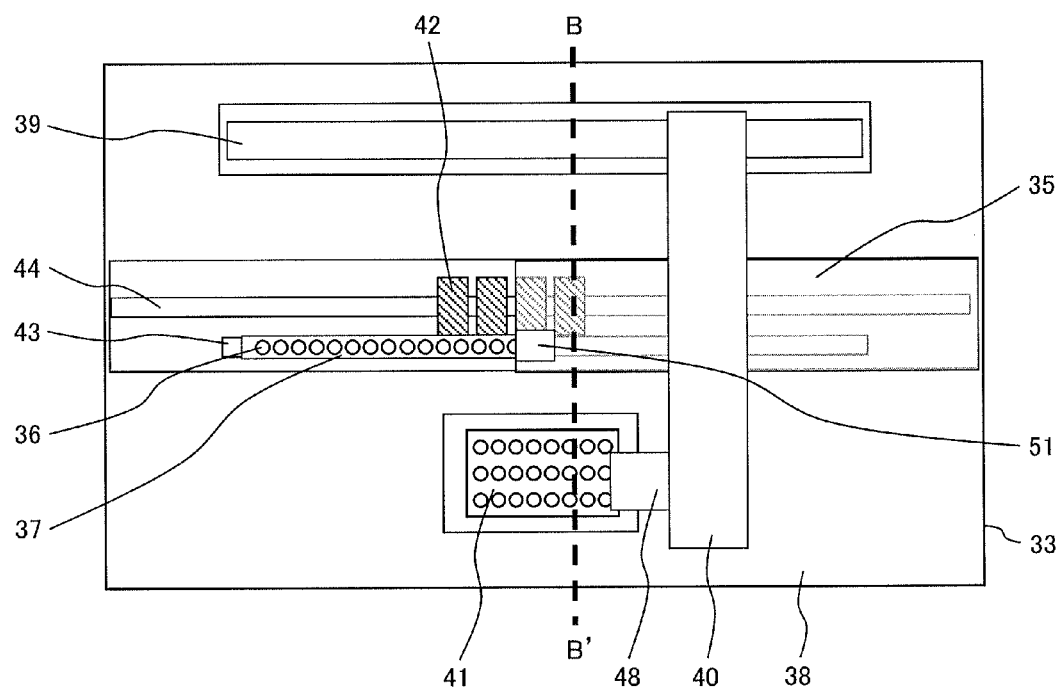
FIG. 9 is a plan view illustrating a configuration of a nucleic-acid amplification detection device of Example 6 of the invention.

FIG. 9 illustrates a configuration different from that of the Example 1, in the embodiment of the invention. A nucleic-acid amplification detection device 33 has a linear loading unit 37, in which a plurality of loading holes 36 for reaction containers are linearly arranged at equal intervals, within a testing section covered with a cover 35 having a loading gate 34. The loading unit includes a thermoregulation unit that may perform thermoregulation for individual loading holes or loading hole groups. An X-axis 39 of a conveyance unit, a Y-axis 40 of the conveyance unit 40, a reaction container rack 41, and a measurement unit 42 are provided in addition to the loading unit on a base 38. The measurement unit 37 is a fluorescent-type measuring instrument as in the Example 1, and is disposed facing the loading unit 37. While the number of the measurement units 42 to be provided varies depending on the number of fluorescent dyes to be detected, one or more measurement units 42 may be provided. In the case where two or more measurement units 42 are provided, the measurement units operate together. The loading unit 37 and the measurement unit 42 can independently perform linear movement operation.

Figures 1, 10:
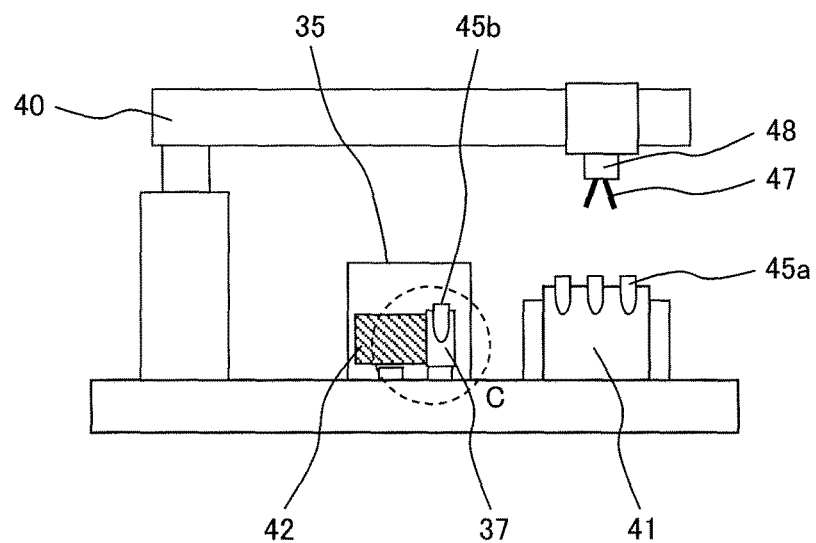
Figures 2, 10:
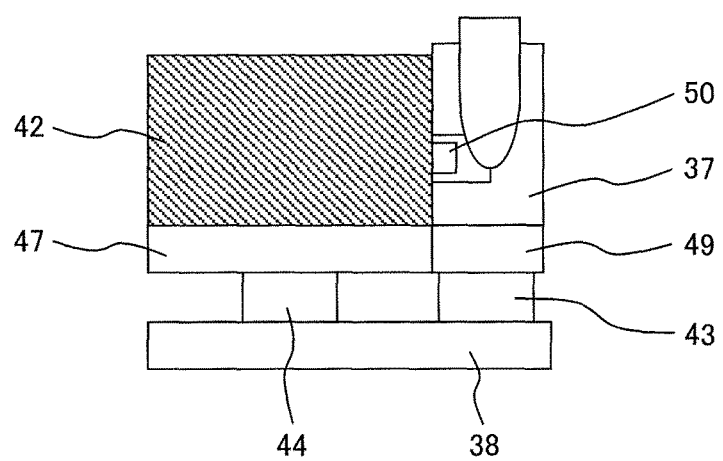

FIG. 10-1 illustrates a side section view of the nucleic-acid amplification detection device 33 according to the Example 6. FIG. 10-2 illustrates a partial enlarged view of the detection section.

A sample-container grasping mechanism 47 moves down by the Z-axis 48 of the conveyance unit 48, catches a reaction container 45a containing a sample from the reaction container rack 41, and introduces the reaction container 45a into the loading unit 37 through a loading gate 51 to load the reaction container into a loading hole 36. The reaction containers 45a can be loaded by the number corresponding to the number of holes 36.

The loading unit 37 is linearly moved on a slide rail 43 of the thermoregulation unit by a drive mechanism 49 formed of a pulse motor, a pulley, and a belt, for example. The one or more measurement units 42 are also linearly moved on a slide rail 44 of the measurement unit by a drive mechanism 46 formed of a pulse motor, and other components. The fluorescent detector 50 performs measurement through a side face of the container. Note that such a measurement method is not limitative, and measurement may be made through a side face of the container. Moreover, the drive mechanism 49 and the drive mechanism 46 may each include any motor other than the pulse motor, or any mechanism other than the combination of the motor and the belt.

The conveyance unit, which is comprised of the X-axis 39 of the conveyance unit, the Y-axis 40 of the conveyance unit, the Z-axis 48 of the conveyance unit, and the sample-container grasping mechanism 47, can access all container placement positions.

In the loading unit 37, one or a group of reaction-container setup holes 36 can be independently subjected to thermoregulation, and thus can be independently controlled to any appropriate temperature. For example, a Peltier device, a heater, or a cooling fan is used for the thermoregulation. Alternatively, a combination of a heat source for heating and a heat source for cooling may be provided, as long as the combination is structured to allow temperature of each of heating and cooling to be controlled to any appropriate temperature.

With measurement operation, the measurement unit and the thermoregulation unit may each have any shape as long as the relative velocity between the measurement unit and the reaction container loaded in the loading unit is maintained constant.

Description is now made on a procedure where reaction containers are continuously introduced/loaded into the loading unit without standby time, and a measurement for detection is made at fixed intervals. This procedure should be similar to that in Example 1. Specifically, relative velocity between a container and the measurement unit during measurement is defined as V3, the velocity of the measurement unit 9 is defined as V4, and the angular velocity of the loading unit 4 is defined as V5. The values of V4 and V5 are then determined such that V3 is constant, and are then used for operation of each of the measurement unit and the loading unit. During transfer of the container to the introduction position, V1 is defined by formula (1).

$$V4=V3+V5 \tag{1}$$

The operation of each of the thermoregulation unit and the measurement unit is controlled while the velocity of each unit is determined. The principle as shown in FIG. 13 is applied to a temporal range for receiving measurement signals and a specific measurement range, as in the Example 1.

According to the above operation, although the device configuration of the Example 6 is different from that of the Example 1, the reaction containers can be continuously loaded while the measurement unit performs measurement in an appropriate period, as in the Example 1.

In addition, as described above, the Example 6 achieves the same function as in the Example 1 though the device configuration is different from that of the Example 1. Hence, the Examples 2, 3, 4, and 5 are also achieved with the configuration of the Example 6.

DESCRIPTION OF REFERENCE NUMERALS AND SIGNS

1: nucleic-acid amplification detection device, 2: cover (half section view), 3: loading hole, 4: loading unit, 5: base, 6: X-axis of conveyance unit, 7: Y-axis of conveyance unit, 8: reaction container rack, 9: measurement unit, 10: central axis, 11*a* and 11*b*: reaction container, 12: measurement unit drive mechanism, 13: sample-container grasping mechanism, 14: Z-axis of conveyance unit, 15: loading unit drive mechanism, 16: loading gate, 17: individual temperature control section, 18: pipetting unit, 19: gripper unit, 20: X-axis of robot-arm, 21: Y-axis of robot-arm, 22: pipetting chip, 23: pipetting chip rack, 24: reaction container rack, 25: nucleic-acid amplification detection section, 26: reaction-solution preparation position, 27: reaction container, 28: reagent container, 29: disposal box, 30: closing unit, 31: agitation unit, 32: fluorescent detector, 33: nucleic-acid amplification detection device, 35: cover (half section view), 36: container setup hole, 37: loading unit, 38: base, 39: X-axis conveyance unit, 40: Y-axis conveyance unit, 41: reagent container rack, 42: measurement unit, 43: loading unit slide rail, 44: measurement unit slide rail, 45*a* and 45*b*: reagent container, 46: measurement unit drive mechanism, 47: sample-container grasping mechanism, 48: Z-axis of conveyance unit, 49: loading unit drive mechanism, 50: fluorescent detector, 51: loading gate

The invention claimed is:

1. A method for detecting nucleic acid amplification, the method comprising:
   (a) loading a new reaction container comprising a sample and a reagent for nucleic acid amplification into an empty loading position in a loading unit;
   (b) simultaneously measuring with a measurement unit a nucleic acid amplification reaction in reaction containers previously loaded into loading positions of the loading unit;
   (c) performing a rotational movement or linear movement of the measurement unit in a predetermined direction relative to the loading unit to sequentially receive a measurement signal from each sample in reaction containers located in the loading unit in a fixed period;
   wherein loading the new reaction container does not interrupt measuring the nucleic acid amplification reaction in reaction containers previously loaded into loading positions of the loading unit;
   wherein the loading unit has a thermoregulation unit;
   wherein the measurement unit faces the loading unit;
   wherein each of the loading unit and the measurement unit has an independent movement mechanism;
   wherein a cover covers the loading unit and comprises a reaction-container loading gate;
   wherein the measurement unit rotation velocity is fixed while the loading unit is making a stop; and
   wherein the measurement unit maintains a relative velocity that is constant with respect to a loading unit rotation velocity when an empty position of the loading unit is moved to the reaction-container loading gate.

2. The method according to claim 1, wherein the thermoregulation unit of the loading unit is set to be controlled by an independent temperature program for each of reaction containers or reaction container groups to be loaded.

3. The method according to claim 1, wherein the thermoregulation unit of the loading unit is set to perform constant temperature control in nucleic acid sequence-based amplification.

4. The method according to claim 1, further comprising:
   setting a temporal range to receive measurement signals from the reaction containers, wherein the temporal range covers a plurality of specific measurement ranges with different time periods which depend on a time period for detecting various samples, and
   setting a measurement-signal receiving period within the temporal range to receive measurement signals, wherein the measurement-signal receiving period covers all the specific measurement ranges by controlling the relative velocity between the loading unit and the measurement unit, and
   selecting a specific measurement range for nucleic-acid amplification detection from the temporal range to receive measurement signals for each reaction container or reaction container group to be loaded into the loading unit, and extracting a measurement signal contained in the selected specific measurement range as measurement data for nucleic-acid amplification detection.

* * * * *